Jan. 6, 1948. W. E. JOHNSON Plant Pat. 777
ROSE PLANT
Filed Dec. 19, 1946
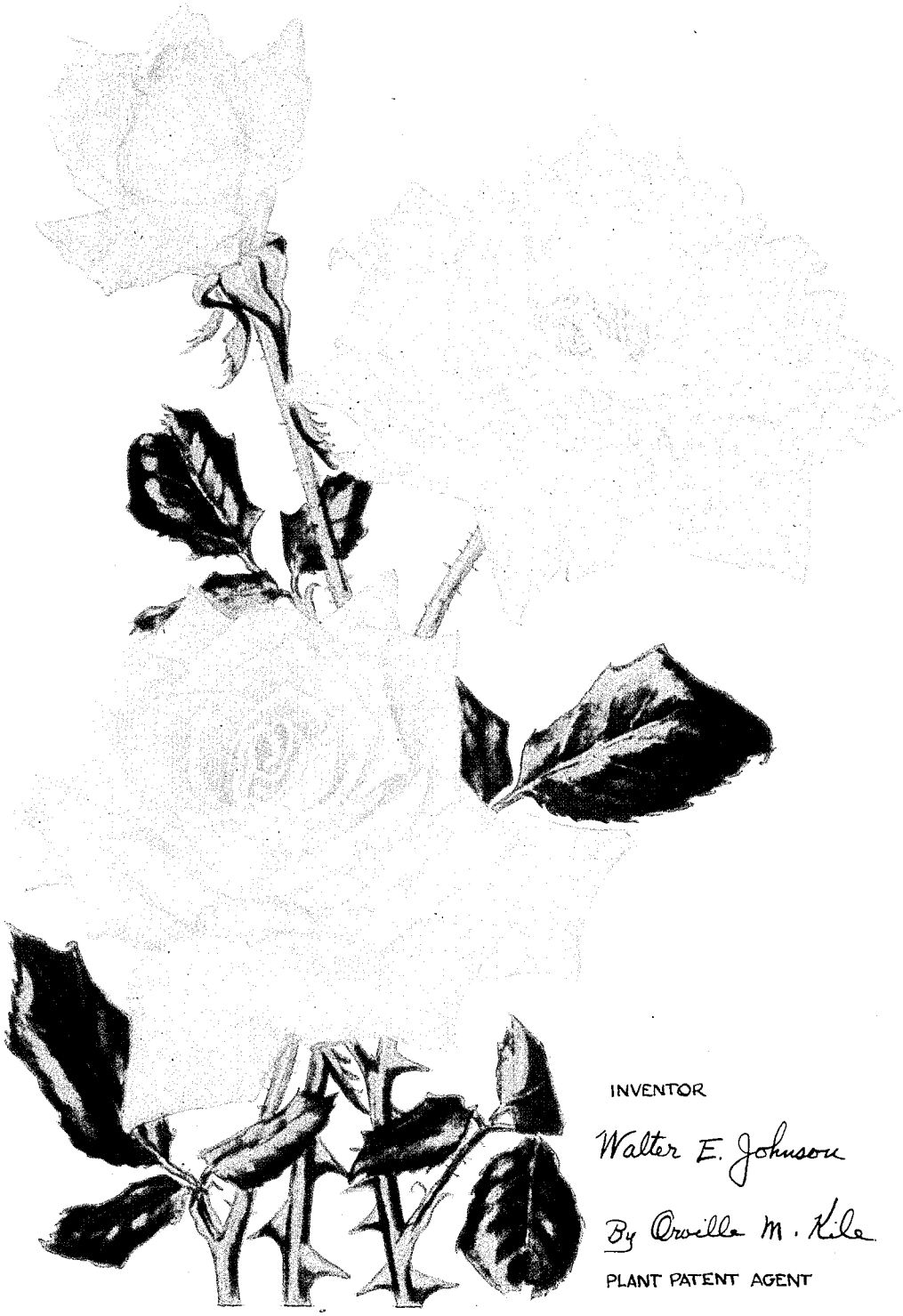
INVENTOR
Walter E. Johnson
By Orville M. Kile
PLANT PATENT AGENT Patented Jan. 6, 1948

Plant Pat. 777

UNITED STATES PATENT OFFICE

777

ROSE PLANT

Walter E. Johnson, Reading, Mass.

Application December 19, 1946, Serial No. 717,205

1 Claim. (Cl. 47—61)

My present discovery relates to a new and useful variety of hybrid tea rose plant with particular reference to the flower borne by the plant. Outstanding among its characteristics are the intense fragrance and the distinctive form and color of its flowers as well as its prolific production habits.

This new variety was discovered by me as a sport of the variety Orange Nassau (Plant Patent 350) at a greenhouse in Reading, Massachusetts. It has been asexually reproduced through several generations, and the distinctive qualities have proved to be firmly fixed.

The accompanying illustrations show in approximately natural colors and in various stages of opening, three specimens of the flower of this new rose plant, together with some of the foliage and stems.

Following is a detailed description of my new variety. Color plate references are to Ridgway's Color Standards and Nomenclature.

*The Plant*

Form: Upright, rounded bush. Very thorny and free-branching.

Growth: Strong and vigorous.

Blooming habit: Excellent producer of good quality flowers through the season.

Disease resistance: Better than average.

Stems: Strong, sturdy and long, holding flowers upright. Bice Green (Plate XVII). Armed with many thorns.

Thorns: Large, stout, broad based, downward pointing, irregularly spaced, usually tinged with deep red.

Foliage:

*Leaflets.*—Three to five.

*Quantity.*—Abundant.

*Size and shape.*—There are two types of foliage. The greater portion is medium sized and oval to ovate in shape, measuring 2½ to 3 inches long and 1½ to 1¾ inches wide (terminal leaflet). The other type, frequently found closest to the flower, is small and broadly obovate. Edges sharply and finely double serrate. Margins usually slightly downward rolled.

*Color.*—Upper surface is dark green (approximately Dark Cress Green, Plate XXXI). Under surface is lighter green, frequently tinged with red.

*Surface aspect.*—Smooth and without gloss.

*Texture.*—Heavy.

*Rachis.*—Grooved above. Tinged with red. Fine spines on under side.

*Stipules.*—Medium in length; sharply pointed; clasping.

*Flower*

Bud:

*Size.*—Large, measuring 1½ to 2 inches long.

*Form.*—Ovoid to tapering.

*Color.*—Grenadine Pink (Plate II).

*Peduncle.*—Short; strong; rigid. Has a few long, fine, downward-pointing prickles irregularly spaced.

*Calyx.*—Urn-shaped, contracted at mouth, becoming fleshy in fruit.

*Sepals.*—Five. Broadly lanceolate; occasionally slightly foliaceous. Tips serrate. Lower margin ciliate. Inner surface gray pubescent; outer surface glabrous. Reflexed when flower is half open. Persistent.

Bloom:

*Size.*—When fully expanded, the average size is 3½ to 4 inches in diameter.

*Borne.*—Singly, on long sturdy stems.

*Form.*—Pointed when first open; inner petals imbricated; outer petals turned backward making a shield shape with one sharp point at top and one to each side, finally recurving into funnel-shape. Center of bloom remains high and closely furled for several days. Finally, the flower opens wide and the petals quill backward, revealing many yellow stamens and pistils.

*Color.*—When the flower is half open the inner petals are Grenadine (Plate II), shading to Grenadine Pink (Plate II) on the outer petals. Inside surface at base is suffused with Apricot Yellow (Plate IV). Petals are Orange Buff (Plate III) at base. As the flower becomes older it lightens in color. Then the outer petals aproach Orient Pink (Plate II) and the inner petals Geranium Pink (Plate I). In the final stages, the color again darkens and the outer petals are between Thulite Pink (Plate XXVI) and Deep Rose Pink (Plate XII).

*Petalage.*—There are twenty-five to thirty large petals, with five to ten small ones.

Petals:

*Shape.*—Broadly ovate. Edges whole. Outer petals almost round when unfurled.

*Size.*—Outer petals measure up to 1¾ inches wide by 2 inches long.

*Texture.*—Fine to medium.

*Fragrance.*—Abundant. Has fruity quality.

*Persistence.*—Petals cling tenaciously.

*Lasting quality.*—Very long-lasting both on the bush and as a cut flower.

Reproductive organs:

*Stamens.*—Many, surrounding pistils. *Filament*—Light Orange Yellow. *Anther*—Deep Chrome (Plate III).

*Pistils.*—Top of *style* is tinged with dull red. *Stigma* is Pinard Yellow (Plate III).

*Comparison*

The variety most like my new variety is the R. M. S. Queen Mary, the subject of Plant Patent No. 249. Principal differences are as follows:

1. There is a greater quantity of foliage on my new variety.

2. The bush of my variety grows more rounded.

3. The leaflets of the foliage of my variety are more rounded.

4. My variety breaks more freely and is much more prolific in its production of flowers. It produces approximately two to one of R. M. S. Queen Mary.

5. Sepals of my variety are more foliaceous.

6. Flowers of my variety are not so large, being medium sized as a rule.

7. Flowers of my new variety are much more fragrant.

8. Petals of flowers of my new variety have a much finer texture.

9. Color of the flowers of the two varieties differs materially.

10. Form of the flowers of the two varieties is very different. (As described in the specifications herewith and in Plant Patent No. 249).

11. Parentage of the two varieties is entirely different.

Having thus disclosed my discovery, I claim:

The new and distinct variety of hybrid tea rose plant, substantially as herein shown and described, characterized particularly by its vigorous growth; study stems; distinctively shaped foliage; free-breaking habit which results in prolific flower production; and very fragrant, fine-textured flowers having distinctive form and coloring, the latter being predominantly Grenadine Pink.

WALTER E. JOHNSON.